United States Patent
Freeman et al.

(10) Patent No.: US 11,654,234 B2
(45) Date of Patent: May 23, 2023

(54) RESPIRATORY PARAMETER GUIDED AUTOMATED IV ADMINISTRATION AND IV TUBE CLAMP ACTIVATION

(71) Applicant: Respiratory Motion, Inc., Waltham, MA (US)

(72) Inventors: Jenny E. Freeman, Weston, MA (US); Michael Lalli, Somerville, MA (US); Jordan Brayanov, Medford, MA (US); Malcolm G. Bock, Medfield, MA (US)

(73) Assignee: Respiratory Motion, Inc., Watertown, MA (US)

( * ) Notice: Subject to any disclaimer, the term of this patent is extended or adjusted under 35 U.S.C. 154(b) by 0 days.

(21) Appl. No.: 14/932,586

(22) Filed: Nov. 4, 2015

(65) Prior Publication Data
US 2016/0184518 A1    Jun. 30, 2016

Related U.S. Application Data

(60) Provisional application No. 62/075,093, filed on Nov. 4, 2014.

(51) Int. Cl.
*A61M 5/172* (2006.01)
*A61M 5/14* (2006.01)
(Continued)

(52) U.S. Cl.
CPC ............ *A61M 5/1723* (2013.01); *A61M 5/14* (2013.01); *A61M 5/142* (2013.01);
(Continued)

(58) Field of Classification Search
CPC ...... A61M 5/1723; A61M 5/14; A61M 5/142; A61M 5/16813; A61M 2230/42;
(Continued)

(56) References Cited

U.S. PATENT DOCUMENTS

| 3,433,217 A | 3/1969 | Rieke et al. |
| 3,690,143 A | 9/1972 | Day et al. |

(Continued)

FOREIGN PATENT DOCUMENTS

| CN | 1034665 | 8/1989 |
| CN | 101496767 | 8/2010 |

(Continued)

OTHER PUBLICATIONS

U.S. Appl. No. 12/677,216, Freeman et al.
(Continued)

*Primary Examiner* — Lauren P Farrar
*Assistant Examiner* — Hamza A Darb
(74) *Attorney, Agent, or Firm* — Remenick PLLC

(57) ABSTRACT

Disclosed is a system that includes a sensor for acquiring a physiological bioelectrical impedance signal from a patient functionally connected to the computing device. The computing device preferably analyzes the physiological bioelectrical impedance signal and provides outputs an assessment of minute ventilation of the patient based on the analyzed bioelectrical impedance signal. Preferably, the system monitors the signal over time, provides a control signal to an IV pump that instructs the IV Pump to automatically adjust medication levels by automatically lowering medication levels when respiration levels fall or completely stopping flow of the medication.

19 Claims, 2 Drawing Sheets

(51) Int. Cl.
*A61M 5/142* (2006.01)
*A61M 5/168* (2006.01)

(52) U.S. Cl.
CPC ..... *A61M 5/16813* (2013.01); *A61M 2205/18* (2013.01); *A61M 2230/005* (2013.01); *A61M 2230/205* (2013.01); *A61M 2230/40* (2013.01); *A61M 2230/42* (2013.01)

(58) Field of Classification Search
CPC ...... A61M 2230/205; A61M 2230/005; A61M 2230/40; A61M 2205/18; A61M 2005/1405; A61M 2005/14208; A61M 2005/1726; A61M 2205/581; A61M 2205/583; A61M 2016/0015; A61M 2016/0027; A61M 2016/003; A61B 5/0809

See application file for complete search history.

(56) References Cited

U.S. PATENT DOCUMENTS

| | | | |
|---|---|---|---|
| 3,742,936 | A | 7/1973 | Blanie et al. |
| 4,036,217 | A | 7/1977 | Ito et al. |
| 5,058,583 | A | 10/1991 | Geddes et al. |
| 5,469,859 | A | 11/1995 | Tsoglin et al. |
| 5,735,284 | A | 4/1998 | Tsoglin et al. |
| 6,168,568 | B1 | 1/2001 | Gavriely |
| 6,173,198 | B1 | 1/2001 | Schulze et al. |
| 6,286,806 | B1 | 9/2001 | Corcoran |
| 6,366,803 | B1 | 4/2002 | Fee |
| 6,402,969 | B1 | 6/2002 | Rodgers et al. |
| 6,809,462 | B2 | 10/2004 | Pelrine et al. |
| 6,976,963 | B2 | 12/2005 | Clift |
| 7,196,317 | B1 | 3/2007 | Meissner, II et al. |
| 7,361,146 | B1 | 4/2008 | Bharmi et al. |
| 7,530,956 | B2 | 5/2009 | Lewicke et al. |
| 8,096,962 | B2 | 1/2012 | Palazzolo et al. |
| 8,306,611 | B2 | 11/2012 | Granov et al. |
| 2002/0032383 | A1 | 3/2002 | Weil et al. |
| 2004/0010207 | A1 | 1/2004 | Flaherty et al. |
| 2004/0071337 | A1 | 4/2004 | Jeung et al. |
| 2004/0123667 | A1 | 7/2004 | McGrath |
| 2005/0033198 | A1 | 2/2005 | Kehyayan et al. |
| 2005/0090753 | A1 | 4/2005 | Goor et al. |
| 2005/0107719 | A1 | 5/2005 | Arad (Abbound) |
| 2005/0113702 | A1 | 5/2005 | Salla et al. |
| 2006/0058600 | A1 | 3/2006 | Eichler |
| 2006/0241506 | A1* | 10/2006 | Melker ............ A61M 16/0069 600/529 |
| 2006/0241513 | A1 | 10/2006 | Hatlestad et al. |
| 2007/0010764 | A1 | 1/2007 | Palazzolo et al. |
| 2007/0060874 | A1* | 3/2007 | Nesbitt ............ A61M 5/14228 604/80 |
| 2007/0276300 | A1 | 11/2007 | Olson et al. |
| 2007/0299389 | A1* | 12/2007 | Halbert ............ A61B 5/0205 604/131 |
| 2008/0262323 | A1* | 10/2008 | Gerber ............ A61B 5/0031 600/301 |
| 2008/0312565 | A1 | 12/2008 | Celik-Butler et al. |
| 2009/0062672 | A1 | 3/2009 | Sly et al. |
| 2009/0149748 | A1 | 6/2009 | Lenhardt et al. |
| 2009/0227849 | A1 | 9/2009 | Goor et al. |
| 2009/0227852 | A1* | 9/2009 | Glaser ............ A42B 3/0433 600/324 |
| 2009/0264789 | A1 | 10/2009 | Molnar et al. |
| 2009/0326253 | A1 | 12/2009 | Iding et al. |
| 2009/0326353 | A1 | 12/2009 | Watson et al. |
| 2010/0049071 | A1 | 2/2010 | Goor et al. |
| 2010/0152600 | A1 | 6/2010 | Droitcour et al. |
| 2010/0228166 | A1 | 9/2010 | Centen |
| 2010/0241181 | A1 | 9/2010 | Savage et al. |
| 2011/0077497 | A1 | 3/2011 | Oster et al. |
| 2011/0245712 | A1 | 10/2011 | Patterson et al. |
| 2011/0306850 | A1 | 12/2011 | Hatlestad et al. |
| 2012/0041279 | A1 | 2/2012 | Freeman et al. |
| 2012/0165883 | A1 | 6/2012 | Kalgren et al. |
| 2013/0023820 | A1 | 1/2013 | Solomon et al. |
| 2013/0187941 | A1 | 7/2013 | Noon |
| 2013/0263855 | A1 | 10/2013 | Tivig et al. |
| 2013/0296823 | A1* | 11/2013 | Melker ............ A61M 5/142 604/503 |
| 2014/0073895 | A1 | 3/2014 | Freeman et al. |

FOREIGN PATENT DOCUMENTS

| | | |
|---|---|---|
| EP | 1302217 | 4/2003 |
| EP | 2008581 | 12/2008 |
| EP | 2018825 | 1/2009 |
| JP | 200070370 | 3/2000 |
| JP | 2007203041 | 8/2007 |
| JP | 2009240752 | 10/2009 |
| WO | WO0033733 | 6/2000 |
| WO | WO2007033025 | 3/2007 |
| WO | WO2007064682 | 6/2007 |
| WO | WO2007147505 | 12/2007 |
| WO | WO2008130549 | 10/2008 |
| WO | WO2009035965 | 3/2009 |
| WO | WO2009036312 | 3/2009 |
| WO | WO2010059049 | 5/2010 |
| WO | WO2011149570 | 12/2011 |

OTHER PUBLICATIONS

U.S. Appl. No. 13/210,360, Freeman et al.
U.S. Appl. No. 13/554,346, Freeman et al.
U.S. Appl. No. 14/021,939, Freeman et al.
PCT Search Report dated Nov. 10, 2008.
PCT Patentability Report dated Nov. 10, 2008.
PCT Patentability Report for PCT/US2011/47812, dated Jan. 10, 2012.
PCT Patentability Report for PCT/US2008/76224, dated Mar. 16, 2010.
PCT Search Report for PCT/US2011/47812, dated Jan. 10, 2012.
PCT Search and Patentability Report for PCT/US12/47604, dated Oct. 12, 2012.
EP Search Report for PCT/US2011/047812, dated Feb. 19, 2014.
PCT Search Report for PCT/US2013/058797, dated Feb. 25, 2014.
EPO Search Report for PCT/US2011/047812, dated Feb. 19, 2014.
Japanese Office Action for PCT/US2011/047812, dated Mar. 2, 2015.
EP Office Action for PCT/US2010/047604, dated Mar. 5, 2015.
EP Office Action for PCT/US2011/47812, dated Mar. 11, 2015.
AU Exam Report for Application No. 2011289159, dated May 21, 2015.
Zulkarneev R Kh. et al., A Hardware-Software System for Volumetric Calibration of Impedance Pneumograms, Biomedical Engineering, vol. 35, No. 1, 2001, pp. 48-51.
PCT Search and Patentability Report for PCT/US2015/19196, dated Jun. 24, 2015.
CL Office Action for Application No. A61B5/091, dated Apr. 22, 2015.
EP Office Action for Application No. 118171792-1657, dated Nov. 4, 2015.
CN Office Action for PCT/US2012/047604, dated Nov. 12, 2015.
IL Office Action for Application No. 223972, dated Dec. 27, 2015.
Pajic, et al, Model-driven safety analysis of closed-loop medical systems, IEEE Trans Industr Inform. vol. 10, pp. 1-35, p. 4, para. 1-2, Oct. 28, 2013.
PCT Search Report for PCT/US15/59032, dated Feb. 4, 2016.
EP Search Report for 15856645.5 dated Nov. 6, 2018.
AU Examination Report for App. No. 2015343123 dated Jul. 23, 2019.

* cited by examiner

RESPIRATORY PARAMETER GUIDED AUTOMATED IV ADMINISTRATION AND IV TUBE CLAMP ACTIVATION

REFERENCE TO RELATED APPLICATIONS

The present application claims priority to Provisional U.S. Application No. 62/075,093, filed Nov. 4, 2014 and entitled "Respiratory Parameter Guided Automated IV Administration and IV Tube Clamp Activation," which is incorporated in its entirety.

BACKGROUND OF THE INVENTION

1. Field of the Invention

This invention is directed to systems and methods of automating administration of fluids with respiratory monitoring.

2. Description of the Background

Patient monitoring is essential for clinical care, playing a critical role in patient therapy by providing a quantitative assessment of patient status. Close monitoring directly contributes to clinical decisions by supplying early warning against emergency degeneration though the provision of continuous information that is relevant to the patient's condition. Physiological scores, such as Acute Physiology and Chronic Health Education (APACHE), Mortality Probability Model (MPM), and Therapeutic Intervention Scoring System (TISS), have shown that monitoring significantly improves patient outcomes. A key weakness of prior art and utilizing pulse oximetry to monitor and track respiration is that it is a very late indicator of a patients breathing. It represents the oxygen level in the blood and does not reflect the actual real time breathing levels of the patient.

It has been demonstrated that, in a person who stops breathing, it can take 5-10 minutes before their SpO2 values fall out of the normal range. While this parameter has been used, it is a late and trailing indicator of respiration adequacy. The idea that continuous IV administration of powerful opiates could be allowed for additional 10 minutes, is not optimal and, in certain situations, could be dangerous. Knowing the instantaneous amount of air which goes in and out of the lungs is the most direct measurement of respiration adequacy.

When analgesic medications are provided to a patient there is a significant risk during the administration period that a patient could have adverse reactions (e.g. overdose or side effects). These can significantly reduce respiration and can lead to respiratory depression, failure, and death. Current infusion/administration products rely on direct monitoring of the patient, by a nurse and/or clinician to ensure the patient is responding appropriately to the medication. An ultimate solution would be to provide a way to automatically stop the administration of medication/treatment/pain killer (Opiates) when the patients respiratory signs (e.g. minute ventilation (MV), tidal volume (TV), respiratory rate (RR), or end tidal $CO_2$ (ETCO2)) vary from normal range.

SUMMARY OF THE INVENTION

The present invention overcomes the problems and disadvantages associated with current strategies and designs and provides new tools and methods for automating administration of fluids with respiratory monitoring.

The system preferably includes a sensor for acquiring a physiological bioelectrical impedance signal from a patient functionally connected to a computing device. The computing device preferably analyzes the physiological bioelectrical impedance signal and provides outputs an assessment of minute ventilation of the patient based on the analyzed bioelectrical impedance signal. Preferably, the system monitors the signal over time, provides a control signal to an IV pump that instructs the IV Pump to automatically adjust medication levels by automatically lowering medication levels when respiration levels fall or completely stopping flow of the medication.

One embodiment of the invention is directed to an automated fluid administration safety device. The device comprises a respiratory parameter monitoring device, a set of sensors adapted to obtain patient data coupled to the respiratory parameter monitoring device, and a fluid delivery system controlled by the respiratory parameter monitoring device and coupled to the patient.

In a preferred embodiment, the fluid delivery system comprises at least one of an IV pump and a tube clamp. Preferably, the respiratory parameter monitoring device adjusts the administration of fluid by at least one of slowing fluid flow through the IV pump or closing the tube clamp. Preferably, fluid flow to the patient is reduced or stopped based on the monitored respiratory parameter. The fluid flow is preferably reduced upon the monitored respiratory parameter reaching a first threshold and fluid flow is stopped upon the monitored respiratory parameter reaching a second threshold.

Preferably, the set of sensors is electrodes and the patient data is changes in impedance. In a preferred embodiment, the respiratory parameter is variability, variation, or complexity in at least one of the patient's minute volume, the patient's respiratory rate, the patient's respiratory pressure, the patient's respiratory flow, a patient's end tidal $CO_2$, the patient's sublingual $CO_2$, the patient's intensity of respiration, the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the patient's impedance and volume signal, variation of phase lag between the patient's impedance and volume signal, the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the subject's impedance and volume signal, variation of phase lag between the subject's impedance and volume signal, and combinations thereof.

Preferably, the device further comprises a self-medication activation button, wherein the self medication activation button is deactivated upon the monitored respiratory parameter reaching a threshold. In a preferred embodiment, the device further comprises at least one of an audible or visual alarm. The fluid is preferably at least one of a medication, saline solution, an antibiotic, blood, a blood substitute, a vitamin, a buffer, or a nutrient.

Another embodiment of the invention is directed to a method of automatically administering fluid to patient. The method comprises the steps of coupling a set of sensors to the patient, obtaining patient data from the set of sensors, monitoring for a respiratory parameter from the patient data on a respiratory parameter monitoring device, coupling a fluid delivery system to the patient, and controlling the fluid delivery system based on the monitored respiratory parameter.

Preferably, the fluid delivery system comprises at least one of an IV pump and a tube clamp. In a preferred embodiment, the respiratory parameter monitoring device adjusts the administration of fluid by at least one of slowing fluid flow through the IV pump or closing the tube clamp. The method preferably, further comprises reducing or stopping fluid flow to the patient based on the monitored respiratory parameter. Preferably, the fluid flow is reduced upon the monitored respiratory parameter reaching a first threshold and fluid flow is stopped upon the monitored respiratory parameter reaching a second threshold.

In a preferred embodiment, the set of sensors is electrodes and the patient data is changes in impedance. Preferably, the respiratory parameter is variability, variation, or complexity in at least one of the patient's minute volume, the patient's respiratory rate, the patient's respiratory pressure, the patient's respiratory flow, a patient's end tidal $CO_2$, the patient's sublingual $CO_2$, the patient's intensity of respiration, the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the patient's impedance and volume signal, variation of phase lag between the patient's imped-ance and volume signal, the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the subject's impedance and volume signal, variation of phase lag between the subject's impedance and volume signal, and combinations thereof.

The method preferably further comprises deactivating a self-medication activation button upon the monitored respiratory parameter reaching a threshold. Preferably, the method further comprises activating at least one of an audible or visual alarm upon the monitored respiratory parameter reaching a threshold. Preferably, the fluid is at least one of a medication, saline solution, an antibiotic, blood, a blood substitute, a vitamin, a buffer, or a nutrient.

Other embodiments and advantages of the invention are set forth in part in the description, which follows, and in part, may be obvious from this description, or may be learned from the practice of the invention.

DESCRIPTION OF THE INVENTION

Figure 1:
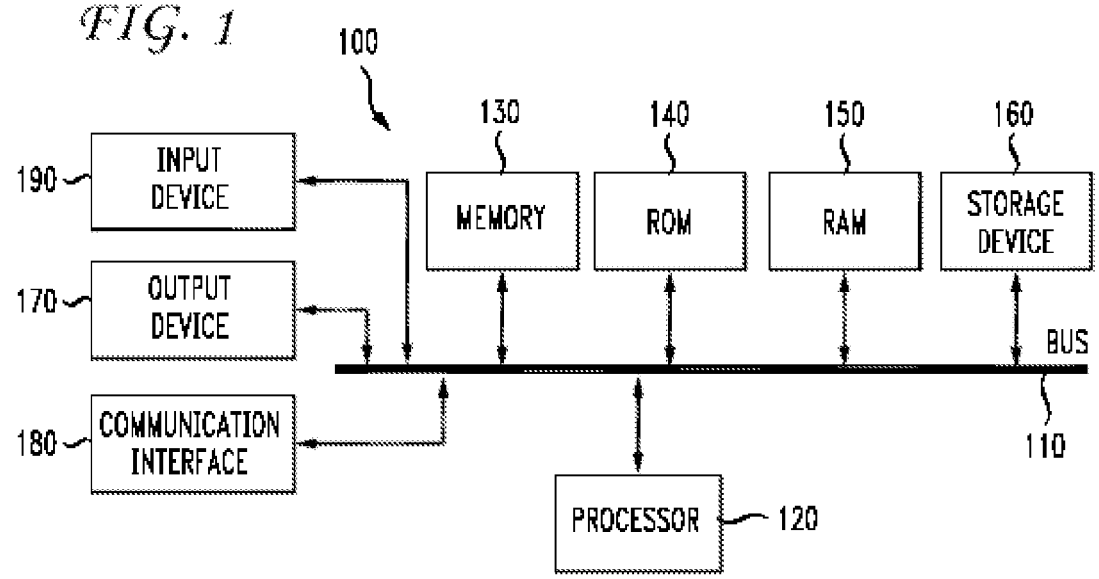
FIG. 1. System setup for collecting impedance and spirometry waveforms simultaneously.

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention With reference to FIG. 1, an exemplary system includes at least one general-purpose computing device 100, including a processing unit (CPU) 120 and a system bus 110 that couples various system components including the system memory such as read only memory (ROM) 140 and random access memory (RAM) 150 to the processing unit 120. Other system memory 130 may be available for use as well. It can be appreciated that the invention may operate on a computing device with more than one CPU 120 or on a group or cluster of computing devices networked together to provide greater processing capability. The system bus 110 may be any of several types of bus structures including a memory bus or memory controller, a peripheral bus, and a local bus using any of a variety of bus architectures. A basic input/output (BIOS) stored in ROM 140 or the like, may provide the basic routine that helps to transfer information between elements within the computing device 100, such as during start-up. The computing device 100 further includes storage devices such as a hard disk drive 160, a magnetic disk drive, an optical disk drive, tape drive or the like. The storage device 160 is connected to the system bus 110 by a drive interface. The drives and the associated computer readable media provide nonvolatile storage of computer readable instructions, data structures, program modules and other data for the computing device 100. The basic components are known to those of skill in the art and appropriate variations are contemplated depending on the type of device, such as whether the device is a small, handheld computing device, a desktop computer, a computer server, a handheld scanning device, or a wireless devices, including wireless Personal Digital Assistants ("PDAs"), tablet devices, wireless web-enabled or "smart" phones (e.g., Research in Motion's Blackberry™, an Android™ device, Apple's iPhone™), other wireless phones, a game console (e.g, a Playstation™, an Xbox™, or a Wii™), a Smart TV, a wearable internet connected device, etc. Preferably, the system is technology agnostic.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment.

To enable user interaction with the computing device 100, an input device 190 represents any number of input mechanisms, such as a microphone for speech, a touch-sensitive screen for gesture or graphical input, keyboard, mouse, motion input, speech, game console controller, TV remote and so forth. The output device 170 can be one or more of a number of output mechanisms known to those of skill in the art, for example, printers, monitors, projectors, speakers, and plotters. In some embodiments, the output can be via a network interface, for example uploading to a website, emailing, attached to or placed within other electronic files, and sending an SMS or MMS message. In some instances, multimodal systems enable a user to provide multiple types of input to communicate with the computing device 100. The communications interface 180 generally governs and manages the user input and system output. There is no restriction on the invention operating on any particular hardware arrangement and therefore the basic features here may easily be substituted for improved hardware or firmware arrangements as they are developed.

For clarity of explanation, the illustrative system embodiment is presented as comprising individual functional blocks (including functional blocks labeled as a "processor"). The functions these blocks represent may be provided through the use of either shared or dedicated hardware, including, but not limited to, hardware capable of executing software. For example the functions of one or more processors presented in FIG. 1 may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large scale integration (VLSI) hardware embodiments, as well as custom VLSI circuitry in combination with a general purpose DSP circuit, may also be provided.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate the preferred embodiments of the invention may be practiced in network computing environments with many types of computer system configurations, including personal computers, handheld devices, multi-processor systems, microprocessor-based or programmable consumer electronics, network PCs, minicomputers, mainframe computers, and the like. Networks may include the Internet, one or more Local Area Networks ("LANs"), one or more Metropolitan Area Networks ("MANs"), one or more Wide Area Networks ("WANs"), one or more Intranets, etc. Embodiments may also be practiced in distributed computing environments where tasks are performed by local and remote processing devices that are linked (either by hardwired links, wireless links, or by a combination thereof) through a communications network, e.g. in the "cloud." In a distributed computing environment, program modules may be located in both local and remote memory storage devices.

Figure 2:
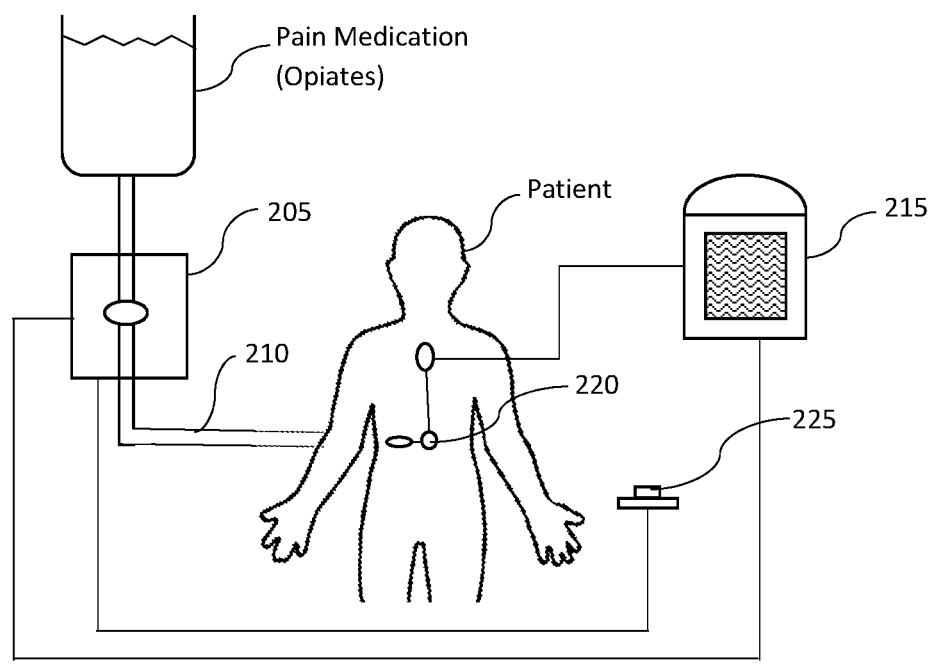
FIG. 2. An embodiment of automated IV pump with feedback from a respiration signal monitor.

One embodiment of the invention is directed to an automated IV pump 205 or tube clamp as depicted in FIG. 2. A tube 210 preferably provides pain medication, however other medication or fluids can be provided by through the tube. For example the tube can provide saline solutions, antibiotics, blood, blood substitutes, vitamins, buffers, or nutrients. Preferably, tube 210 is coupled to the patient by a hypodermic needle, a peripheral cannula, a central line, an implantable port, or another coupling. Preferably, the IV pump 205 or tube clamp is controlled by respiration monitor signals (e.g. impedance minute ventilation or ETCO2 (end tidal CO2)). Preferably, the respiration signals are monitored by a monitoring device 215. Abnormal signals might be abnormal respiration (e.g. low minute ventilation (L/min) or high ETCO2 (mmHg, kPa, %)). Preferably, the signal would activate to slow IV administration or tighten the tube clamp (thereby allowing less fluid through the tube). The IV pump is preferably adjusted based on the respiratory signal. Alternately, the tube that provides medication could be pinched closed. This would halt or slow the flow of the medication. An alarm signal might be triggered and nurse or other medical practitioner would preferably arrive and see the alarming monitor signals and the tube in a closed sealed safe position. Preferably, the medical practitioner would adjust the devices or fluids as needed or perform any necessary medical procedures.

The automated IV pump 205 preferably receives signal from a respiration volume monitor 215, the pump 205 is controlled based on the level of respired air by the patient which is preferably monitored by a set of electrodes 220 attached to the skin of the torso of the patient. The set of electrodes 220 can include one or more electrodes capable of transmitting and/or receiving an electronic signal. For example, the electrodes 220 may detect the impedance across the torso of the patient. As the patient breaths in and the chest expands, the impedance of the patient changes. Such changes in impedance can be measured by monitor 215. Based on the changes in impedance, respiratory parameters can be determined. For example, the respiratory parameters may be variability, variation, or complexity in at least one of the patient's minute volume, the patient's respiratory rate, the patient's respiratory pressure, the patient's respiratory flow, a patient's end tidal CO2, the patient's sublingual CO2, the patient's intensity of respiration, the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the patient's impedance and volume signal, variation of phase lag between the patient's impedance and volume signal, the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the subject's impedance and volume signal, variation of phase lag between the subject's impedance and volume signal, and combinations thereof.

If the respiratory parameters is normal then the pain medication can continue on a standard dosage. When a monitored respiratory parameter drops below a set level of the normal range (e.g. 80%) for a person of that weight or other demographic, then the pump 205 will preferably reduce the rate of medication administration. If the respiration parameter goes below a further threshold (e.g. 40%) then the administration of the fluid is preferably stopped. IV administration can be resumed once the respiration parameter returns back above a certain level (e.g. 80% of normal expected). Preferably, the reduction, stoppage, and resumption of IV administration is automatic.

Another aspect of the invention is once the respiration level goes below a reference level, such as about 60% of normal range, then the patient's self medication activation button 225 will preferably be disabled until the respiration level returns above 80%. This will preferably provide a "smart" override to a patient who is very pain sensitive and does not realize the consequences of additional self doses.

Figure 3:
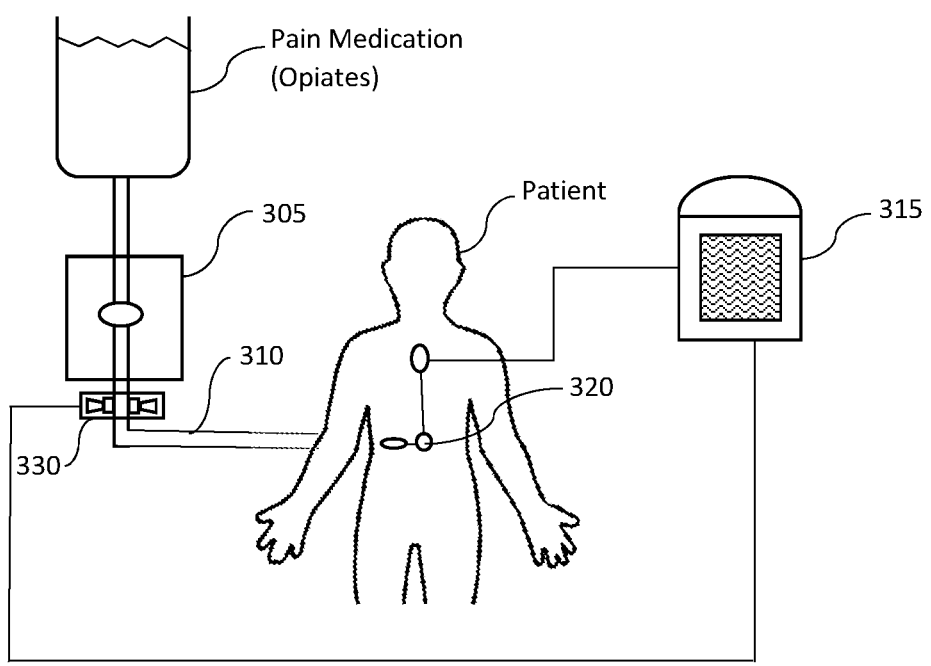
FIG. 3. An embodiment of an automated safety tube clamp.

Another embodiment of the invention is directed to an automated safety tube clamp 330, as depicted in FIG. 3. The clamp 330 preferably receives signal from a respiration volume monitor 315, the clamp 330 is preferably controlled based on the level of respired air by the patient, which is monitored by a set of electrodes 320 preferably attached to the skin of the torso of the patient. A tube clamp 330 is preferably placed around the tube, downstream of a pump 305, at beginning of a procedure and/or therapy session. The clamp 330 is normally open at beginning of procedure when the patient vital signs are normal. For example, if the minute volume is normal then the pain medication can continue on a standard dosage. When minute volume drops below a set level of the normal range (e.g. 40%) for a person of that weight or other demographic, then the clamp will cutoff administration of IV pain medication.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference, including, but not limited to U.S. Patent Application Publication Nos. 2010/0324437, 2012/0041279, 2013/0023781, 2014/0073895, and 2015/0254880. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:
1. An automated fluid administration safety device, comprising:

an impedance-based respiratory volume monitoring device;

at least one external sensor adapted to be placed on a patient and couple the patient to the impedance-based respiratory volume monitoring device, the external sensor adapted to monitor impedance data from the patient, wherein the impedance-based respiratory volume monitoring device converts the monitored impedance data into respiratory volume data;

a fluid delivery system controlled by the respiratory volume monitoring device and coupled to the patient, wherein the fluid delivery system provides fluid to the patient based on changes in the respiratory volume data of the patient; and a self-medication button coupled to the fluid delivery system and adapted to provide a dose of medication to the patient upon triggering of the button, wherein the self-medication button is deactivated upon the respiratory volume dropping below a first threshold and reactivating upon the respiratory volume exceeding a second threshold.

2. The automated fluid administration safety device of claim 1, wherein the fluid delivery system comprises at least one of an IV pump and a tube clamp.

3. The automated fluid administration safety device of claim 2, wherein the respiratory volume monitoring device adjusts administration of fluid by at least one of slowing fluid flow through the IV pump or closing the tube clamp.

4. The automated fluid administration safety device of claim 1, wherein fluid flow to the patient is reduced or stopped based on the respiratory volume.

5. The automated fluid administration safety device of claim 4, wherein the fluid flow is reduced upon the respiratory volume reaching the first threshold and fluid flow is stopped upon the monitored respiratory volume reaching the second threshold.

6. The automated fluid administration safety device of claim 1, wherein the at least one sensor comprise a set of electrodes.

7. The automated fluid administration safety device of claim 1, wherein the respiratory volume monitoring device computes variability, variation, or complexity in at least one of a minute volume of the patient, a respiratory rate of the patient, a respiratory pressure of the patient, a respiratory flow of the patient, an end tidal $CO_2$ of the patient, a sublingual $CO_2$ of the patient, an intensity of respiration of the patient, a respiratory curve, change in a shape of respiratory curve of the patient, a respiratory curve based on an inhaled volume of the patient, a respiratory curve based on an exhaled volume of the patient, a respiratory curve based on an inhaled pressure of the patient, a respiratory curve based on an exhaled pressure of the patient, a respiratory curve based on an inhaled flow of the patient, a respiratory curve based on an exhaled flow of the patient, a respiratory curve based on motion of a chest of the patient as measured by imaging, a respiratory curve based on motion of the chest of the patient as measured by contact sensors placed on the chest of the patient, a respiratory curve based on motion of an abdomen of the patient as measured by imaging, a respiratory curve based on motion of the abdomen of the patient as measured by contact sensors placed on the abdomen of the patient, a respiratory curve based on motion of both the chest and abdomen of the patient as measured by imaging, a respiratory curve based on motion of the chest and abdomen of the patient as measured by contact sensors placed on the chest and abdomen of the patient, variation of interbreath intervals of the patient, phase lag between an impedance and volume signal, variation of phase lag between the patient's impedance and volume signal of the patient, an respiratory curve of the patient, change in the shape of the respiratory curve of the patient, a respiratory curve based on inhaled volume of the patient, a respiratory curve based on exhaled volume of the patient, a respiratory curve based on inhaled pressure of the patient, a respiratory curve based on exhaled pressure of the patient, a respiratory curve based on inhaled flow of the patient, a respiratory curve based on exhaled flow of the patient, a respiratory curve based on motion of the chest of the patient as measured by imaging, a respiratory curve based on motion of the chest of the patient as measured by contact sensors placed on the chest of the patient, a respiratory curve based on motion of the abdomen of the patient as measured by imaging, a respiratory curve based on motion of the abdomen of the patient as measured by contact sensors placed on the abdomen of the patient, a respiratory curve based on motion of both the chest and abdomen of the patient as measured by imaging, a respiratory curve based on motion of the chest and abdomen of the patient as measured by contact sensors placed on the chest and abdomen of the patient, variation of interbreath intervals of the patient, phase lag between impedance and volume signal of the patient, variation of phase lag between impedance and volume signal of the patient, and combinations thereof.

8. The device of claim 7 where the computed changes in variability, variation, or complexity of the respiratory volumes controls the fluid delivery system.

9. The automated fluid administration safety device of claim 1, further comprising at least one of an audible or visual alarm.

10. The automated fluid administration safety device of claim 1, wherein the fluid is at least one of a medication, saline solution, an antibiotic, blood, a blood substitute, a vitamin, a buffer, or a nutrient.

11. A method of automatically administering fluid to patient, comprising:

coupling at least one external sensor of an impedance-based respiratory volume monitoring device to the patient;

obtaining impedance data from the at least one sensor;

converting the impedance data into respiratory volume data;

monitoring for changes in respiratory volumes from the impedance data on the impedance-based respiratory volume monitoring device;

coupling a fluid delivery system to the patient;

controlling the fluid delivery system based on the changes in respiratory volume; and deactivating a self-medication button upon the respiratory volume dropping below a first threshold and reactivating the self-medication button upon the respiratory volume exceeding a second threshold.

12. The method of claim 11, wherein the fluid delivery system comprises at least one of an IV pump and a tube clamp.

13. The method of claim 12, wherein the respiratory volume monitoring device adjusts administration of fluid by at least one of slowing fluid flow through the IV pump or closing the tube clamp.

14. The method of claim 11, further comprising reducing or stopping fluid flow to the patient based on the monitored respiratory volume.

15. The method of claim 14, wherein the fluid flow is reduced upon the monitored respiratory volume reaching the first threshold and fluid flow is stopped upon the monitored respiratory volume reaching the second threshold.

16. The method of claim 11, wherein the at least one sensor comprise a set of electrodes.

17. The method of claim 11, further comprising monitoring for variability, variation, or complexity in at least one of a minute volume of the patient, a respiratory rate of the patient, a respiratory pressure of the patient a respiratory flow of the patient, an end tidal CO2 of the patient, a sublingual CO2 of the patient, an intensity of respiration of the patient, a respiratory curve, change in a shape of respiratory curve of the patient, a respiratory curve based on an inhaled volume of the patient, a respiratory curve based on an exhaled volume of the patient, a respiratory curve based on an inhaled pressure of the patient, a respiratory curve based on an exhaled pressure of the patient, a respiratory curve based on an inhaled flow of the patient, a respiratory curve based on an exhaled flow of the patient, a respiratory curve based on motion of a chest of the patient as measured by imaging, a respiratory curve based on motion of the chest of the patient as measured by contact sensors placed on the chest of the patient, a respiratory curve based on motion of an abdomen of the patient as measured by imaging, a respiratory curve based on motion of the abdomen of the patient as measured by contact sensors placed on the abdomen of the patient, a respiratory curve based on motion of both the chest and abdomen of the patient as measured by imaging, a respiratory curve based on motion of the chest and abdomen of the patient as measured by contact sensors placed on the chest and abdomen of the patient, variation of interbreath intervals of the patient, phase lag between an impedance and volume signal, variation of phase lag between the patient's impedance and volume signal of the patient, an respiratory curve of the patient, change in the shape of the respiratory curve of the patient, a respiratory curve based on inhaled volume of the patient, a respiratory curve based on exhaled volume of the patient, a respiratory curve based on inhaled pressure of the patient, a respiratory curve based on exhaled pressure of the patient, a respiratory curve based on inhaled flow of the patient, a respiratory curve based on exhaled flow of the patient, a respiratory curve based on motion of the chest of the patient as measured by imaging, a respiratory curve based on motion of the chest of the patient as measured by contact sensors placed on the chest of the patient, a respiratory curve based on motion of the abdomen of the patient as measured by imaging, a respiratory curve based on motion of the abdomen of the patient as measured by contact sensors placed on the abdomen of the patient, a respiratory curve based on motion of both the chest and abdomen of the patient as measured by imaging, a respiratory curve based on motion of the chest and abdomen of the patient as measured by contact sensors placed on the chest and abdomen of the patient, variation of interbreath intervals of the patient, phase lag between impedance and volume signal of the patient, variation of phase lag between impedance and volume signal of the patient, and combinations thereof.

18. The method of claim 11, further comprising activating at least one of an audible or visual alarm upon the respiratory volume reaching the first threshold or the second threshold.

19. The method of claim 11, wherein the fluid is at least one of a medication, saline solution, an antibiotic, blood, a blood substitute, a vitamin, a buffer, or a nutrient.

\* \* \* \* \*